United States Patent [19]

Lisowsky

[11] Patent Number: 5,543,535

[45] Date of Patent: Aug. 6, 1996

[54] ORGANOTIN COMPOUNDS USEFUL IN PREPARING BRIDGED STEREORIGID METALLOCENES

[75] Inventor: Richard Lisowsky, Kamen, Germany

[73] Assignee: Witco GmbH, Bergkamen, Germany

[21] Appl. No.: 392,389

[22] Filed: Feb. 22, 1995

[30] Foreign Application Priority Data

Feb. 25, 1994 [DE] Germany ............... 44 06 109.9

[51] Int. Cl.[6] ............... C07F 7/22
[52] U.S. Cl. ............... 556/11; 556/12; 556/87; 556/28; 556/95
[58] Field of Search ............... 556/95, 87, 11, 556/12, 28

[56] References Cited

FOREIGN PATENT DOCUMENTS

| | | |
|---|---|---|
| 0344887 | 12/1989 | European Pat. Off. . |
| 622826 | 2/1991 | European Pat. Off. . |
| 0416815 | 3/1991 | European Pat. Off. . |
| 0420436 | 4/1991 | European Pat. Off. . |
| 0480390 | 4/1992 | European Pat. Off. . |
| 0520732 | 12/1992 | European Pat. Off. . |
| 0530908 | 3/1993 | European Pat. Off. . |

OTHER PUBLICATIONS

Wild, et al. "ansa—Metallocene Derivatives VII*Synthesis and Crystal Structure of a Chiral ansa—Zirconocene Derivative With Ethylene–Bridged Tetrahydroindenyl Ligands.", Journal of Organometallic Chemistry, vol. 288 (1985) pp. 63–67.

Collins, et al., "X–Ray Structures of Ethylenebis(Tetrahydroindenyl)–Titanium and –Zirconium Dichlorides: a revision.", Journal of Organometallic Chemistry, vol. 342 (1988) pp. 21–29.

*Primary Examiner*—Porfirio Nazario-Gonzales
*Attorney, Agent, or Firm*—Scully, Scott, Murphy & Presser

[57] ABSTRACT

The invention relates to new bridged organotin compounds useful in preparing bridged stereorigid metallocenes via organomagnesium and organotin compounds.

8 Claims, No Drawings

ORGANOTIN COMPOUNDS USEFUL IN PREPARING BRIDGED STEREORIGID METALLOCENES

BACKGROUND OF THE INVENTION

The invention relates to a new and improved process for preparing bridged stereorigid metallocenes via organomagnesium and organotin compounds.

Metallocenes based on cyclopentadiene, indene and fluorene are, in combination with specific cocatalysts such as, for example, aluminoxanes or tetraphenylborate complexes, highly active catalysts and with suitable ligand systems also form stereospecific catalyst systems for the polymerization of olefins.

These catalysts, processes for their preparation and their use are described in detail in EP-A- 0 480 390, EP-A-0 413 326, EP-A-0 530 908, EP-A-0 344 887, EP-A 420 436, EP-A-0 416 815, and EP-A-0 520 732.

The compounds specified therein are largely produced in accordance with the reaction scheme given, for example, in EP-A-0 480 390, page 5. In this method, the cyclopentadienyl derivatives are metallated with lithium alkyls, subsequently reacted with alkyl dihalides or alkyl ditosylates to give the bridged ligand systems and then, in a subsequent step, reacted again with lithium alkyls to give the corresponding dimetallated compounds which then react with transition metal halides to give the bridged metallocenes (J. Organomet. Chem., 1985, 288, 63; J. Organomet. Chem., 1988, 342, 21).

These processes have a series of disadvantages:

multistage syntheses in which the intermediates sometimes have to be isolated and purified, it is necessary to carry out individual reaction steps at temperatures $\leq 56°$ C., use of solvents which are not unproblematical in terms of safety and/or environmental considerations, such as ether, hexamethylphosphoramide (HMPA), methylene chloride or chloroform, separation processes (e.g. extractions), particularly in the last step, which in combination with the material properties of the products (sparing solubility, extreme sensitivity to traces of air and moisture) and the salts to be separated off (e.g. LiCl) can only be carried out industrially at high cost and contribute to high losses in yield, control of the rac:meso ratio during the synthesis in the case of compounds which, owing to the ligand substitution, can in principle be formed in a racemate (rac) (two enantiomers) and a meso form, is not generally possible (hitherto the formation of the meso compound could be reduced or prevented only by working at $-56°$ C. in a few individual cases), only small yields of the desired metallocene, particularly when calculated over all steps.

Therefore there is increasing interest in the provision of suitable, general synthetic processes, particularly also those which can be used without problems for industrial amounts, which are able to give such transition metal complexes in high yields as cheaply as possible.

It is an object of the invention to derive synthetic processes which allow, while avoiding the indicated disadvantages, the preparation of bridged stereorigid metallocenes in high yields, as a matter of choice with or preferably without isolation of the intermediates, and can also be carried out industrially without problems.

BRIEF SUMMARY OF THE INVENTION

It has now been found that, using dialkylmagnesium compounds, bridged ligand systems can be successfully formed in high yields under industrially advantageous reaction conditions, and also the magnesium and tin derivatives of these ligand systems which are particularly suitable for the optimum further reactions are obtainable in yields in a single-vessel process and can be reacted directly to give the desired metallocenes.

Furthermore, it has surprisingly been found that in reactions of ligands which, owing to their substitution, are suitable for the formation of the stereoisomeric products (racemate (rac):meso compounds), to give metallocenes, it is possible to influence the rac:meso product ratio within wide limits by means of the reaction procedure.

One aspect of the subject matter of the invention is a process for preparing bridged, stereorigid metallocenes of the general formula (1)

$$Q(CPR_a)(Cp'R'_{a'})M(X)_n \qquad (1)$$

wherein Cp is a cyclopentadienyl, an indenyl or a fluorenyl radical;

R and R' are identical or different and each is an alkyl, alkoxy, phosphine, amino, alkylamino, dialkylamino, alkoxy-alkyl, arylalkyl, or aryloxy-alkyl group;

$0 \leq a \leq 4$ and $0 \leq a' \leq 4$;

Cp' is cyclopentadienyl, indenyl, or fluorenyl, or when a' is 1, Cp' can be NR" wherein R" is a $C_1$–$C_{12}$ alkyl or $C_6$–$C_{10}$ aryl radical;

Q is a single-membered or multi-membered bridge

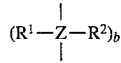

between Cp and Cp' wherein $R^1$ and $R^2$ are identical or different and in each occurrence is a hydrogen atom, a $C_1$–$C_{10}$-alkyl group or a $C_6$–$C_{10}$-aryl group, Z is carbon, silicon or germanium, and b is 1, 2 or 3;

M is a transition metal from any of the groups 3 to 6 of the Periodic Table (IUPAC notation), in particular Zr or Hf;

X is halogen, in particular Cl or Br; and n is the oxidation state of M in said compound, reduced by 2.

Compounds of formula (1) wherein $CpR_a$ and $Cp'R'_{a'}$ in formula (1) are identical, that is, compounds of the formula $Q(CpR_a)_2M(X)_n$ are prepared by a process which comprises 1) in a first step reacting a compound of the formula $CpR_a$ with one or more magnesium compounds of the formula $(R^3R^4)_cMg$, wherein $R^3$ and $R^4$ are each bonded to the Mg and are identical or different and each is H or a $C_1$–$C_{12}$-alkyl radical and c is 0 or 1, in accordance with the general equation $$2CpR_a + (R^3R^4)_cMg \rightarrow (CpR_a)_2Mg + cR^3H + cR^4H$$

and then 2) in a second step, reacting the reaction product of the first step with one or more compounds of the formula $X^1QX^2$, wherein $X^1$ and $X^2$ are identical or different and each is Cl, Br, I or $-OSO_2R^5$, wherein $R^5$ is an alkyl radical having 1–10 carbon atoms or an aryl radical having 6–10 carbon atoms, in accordance with the general equation $$(CpR_a)_2Mg + X^1QX^2 \rightarrow (CpR_a)_2Q + MgX^1X^2$$

and then 3) in a third step, reacting the reaction product of the second step with one or more magnesium compounds of the formula $(R^3R^4)_c Mg$ in accordance with the general equation $$(CpR_a)_2Q + (R^3R^4)_cMg \rightarrow Q(CpR_a)_2Mg + cR^3H + cR^4H$$

and then 4) in a fourth step, reacting the reaction product of the third step with one or more tin compounds of the formula $R_{4-k}{}^6SnX_k{}^3$, wherein $R^6$ is a $C_2$–$C_{20}$-alkyl radical, in particular a $C_4$–$C_8$-alkyl radical, or a $C_6$–$C_{10}$-aryl radical, $X^3$ is a halogen atom, in particular Cl or Br, and k is 1–4, in accordance with the general equation $$Q(CpR_a)_2Mg + 2\ R_{4-k}{}^6SnX_k{}^3 \rightarrow Q(CpR_a)_2(SnX_{k-1}{}^3R_{4-k}{}^6)_2 + MgX_2{}^3$$

and then 5) in a fifth step, reacting the reaction product of the fourth step with a transition metal halide of the formula $M(X)_m$, where m is equal to the oxidation state of M, in accordance with the equation $$Q(CpR_a)_2(SnX_{k-1}{}^3R_{4-k}{}^6)_2 + M(X)_m \rightarrow Q(CpR_a)_2M(X)_2 + 2\ SnX_{k-1}{}^3XR_{4-k}{}^6$$

Compounds of formula (1) wherein CpRa and Cp'R'$_{a'}$ are not identical are prepared by carrying out the aforementioned third, fourth and fifth steps using a compound of the formula Q(CpRa)(Cp'R'$_{a'}$) in place of a compound of the formula Q(CpRa)$_2$.

A further subject matter of the invention is characterized in that the reaction products of the intermediate steps are, without isolation, used directly for the further reaction of the respective subsequent steps.

A further subject matter of the invention is compounds of the general formula $$Q(CpR_a)\ (Cp'R'_{a'})\ (SnX_{k-1}{}^3R_{4-k}{}^6)_2$$

wherein

Q is a single-membered or multi-membered bridge

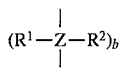

between Cp and Cp', wherein each $R^1$ and $R^2$ are identical or different and each is a hydrogen atom, a $C_1$–$C_{10}$ alkyl group or a $C_6$–$C_{10}$ aryl group, Z is carbon, silicon or germanium, and b is 1, 2 or 3; $0 \leq a \leq 4$ and $0 \leq a' \leq 4$;

Cp and Cp' are each a cyclopentadienyl, an indenyl or a fluorenyl radical;

R and R' are the same or different and in each occurrence is an alkyl, alkoxy, phosphine, amino, alkylamino, dialkylamino, alkoxy-alkyl, aryl-alkyl, or aryloxy-alkyl group;

$R^6$ is a $C_2$–$C_{20}$-alkyl radical or a $C_6$–6 $C_{10}$-aryl radical;

k is 1–4; and $X^3$ is a halogen atom, especially Br or Cl.

Referring to the $R^1$ and $R^2$ substituents, each is preferably $C_1$–$C_5$ alkyl, particularly methyl or ethyl, or is preferably $C_6$–$C_8$ aryl, particularly phenyl.

Referring to the R and R' substituents, each one can be alkyl containing 1 to 10 carbon atoms, for example methyl and ethyl (including dimethyl and trimethyl);

alkoxy containing 1 to 10 carbon atoms, for example methoxy and ethoxy (including dimethoxy and trimethoxy);

alkylamino and/or dialkylamino, wherein each alkyl group contains 1 to 10 carbon atoms, for example dimethylamino and dipropylamino (including bis(dimethylamino));

alkoxyalkyl containing a total of 2 to 20 carbon atoms;

aryl-alkyl and/or aryloxy-alkyl groups wherein the aryl group contains 6 to 10 carbon atoms and the alkyl portion contains 1 to 10 carbon atoms;

phosphine, including phosphine substituted with 1 or 2 groups each of which is $C_1$–$C_{10}$ alkyl or $C_6$–$C_{10}$ aryl, for example diphenylphosphino.

The further subject matter of the invention is characterized by the claims.

DETAILED DESCRIPTION OF THE INVENTION

The cyclopentadienyl compounds $CpR_a$ which can be used according to the invention for the first step 1) of the process are part of the known prior art and are compounds in which Cp can be a cyclopentadienyl radical or an indenyl radical and each of the R groups, if present, is an alkyl, phosphine, amino, alkylamino, dialkylamino, alkoxyalkyl, aryl-alkyl, or aryloxy-alkyl groups with $0 \leq a \leq 4$. Each of the substituents R on the Cp radical can be identical or different. According to the invention, preference is given to compounds in which R represents alkyl radicals having 1–6 carbon atoms and a is 0 to 4.

The compounds $(R^3R^4)_cMg$ used are preferably those in which $R^3$ and $R^4$ are identical or different and each is H or a $C_1$–$C_{12}$ alkyl radical and c is 1. According to the invention, preference is given to butylethylmagnesium, di-n-butylmagnesium, di-n-hexylmagnesium, and n-butyl-sec-butylmagnesium in their commercial formulations and in particular, BOMAG®-A from Witco GmbH (a mixture of dibutylmagnesium, dioctylmagnesium, and optionally, butyloctylmagnesium, in a ratio of butyl:octyl chains of 3:1, 20% strength in heptane).

The reactions are carried out in an inert gas atmosphere such as nitrogen. According to the invention, the components are here preferably initially charged at room temperature in an inert solvent and the temperature is increased with vigorous stirring.

Inert solvents which can be used are those customary in this field such as, for example, aliphatic or cyclic ethers or aromatic hydrocarbons.

According to the invention, preference is given to aliphatic hydrocarbons having boiling points $\leq 60°$ C., preferably $\leq 80°$ C., in particular in the range of 90°–120°. To achieve practical reaction times, the reaction is preferably carried out at the boiling point of the solvents, in particular between 80°–120° C. The concentration of the reaction mixture is largely non-critical. However, to achieve high space-time yields, it is carried out in the upper technically possible range.

The $(CpR_a)_2Mg$ compounds thus obtained are, according to the invention, reacted, preferably directly, in a second stage with the compounds $X^1QX^2$ in accordance with the general reaction equation $$(CpR_a)Mg + X^1QX^2 \rightarrow (CpR_a)_2Q + MgX^1X^2$$

to give the bridged biscyclopentadienyl compounds.

The components $X^1QX^1$ which can be used for bridging are compounds known from the prior art (EP-A-0 480 390, EP-A-0 413 326, EP-A-0 530 908, EP-A-0 344 887). According to the invention, preference is given to compounds in which $X^1$ and $X^2$ are Cl, Br or —O-tosyl.

The reaction mixture of the first step is, if desired, cooled prior to addition of the component $X^1QX^2$ to below the boiling point thereof and after addition is complete is again heated up to the boiling point.

If desired, to increase the reaction rate, ether such as preferably alkyl ether having, in particular, from 6 to 10 carbon atoms such as, in particular, di-n-butyl ether can be additionally added in at most the stoichiometric amount, based on magnesium.

The reaction times are usually between 1 and 3 hours.

In the process of the invention, the starting materials are preferably used in stoichiometric amounts in both steps. As a result of this and the almost quantitative conversion under practical conditions, the bridged biscyclopentadienyl compounds are formed in such purities that they can be used directly without workup for further reactions.

Examples of the bridged biscyclopentadienyl compounds which can be prepared by the process of the invention are dimethylsilyl bis(1-indene), dimethylsilyl-bis (1-cyclopentadiene), 2,2-propylbis(1-indene), 2,2-propylbis (trimethylcyclopentadiene), 2,2-propylbis (5-dimethylamino-1-indene), 2,2-propylbis (6-dipropylamino-1-indene), 2,2-propylbis (4–7-bis (dimethylamino-1-indene)), 2,2-propylbis (5-diphenylphosphino- 1-indene), 2,2-propyl-bis (4,5,6,7-tetrahydro- 1-indene), 2,2-propylbis (4-methyl-1-indene), 2,2-propylbis (5-methyl-1-indene), 2,2-propylbis (6-methyl-1-1-indene), 2,2-propylbis (7-methyl- 1-indene), 2,2-propylbis (5-methoxy-1-indene), 2,2-propylbis (4,7-dimethoxy-1-indene), 2,2-propylbis (2,3-dimethyl-1-indene), 2,2-propylbis (4,7-dimethyl-1-indene, 2,2-propylbis (1-cyclopentadiene), 2,2-propylbis (1-indene), di-phenylmethylbis (1-indene), diphenylmethylbis (1-cyclopentadiene), diphenylmethylbis (1-indene), diphenylsilyl-bis (1-indene), diphenylsilylbis (1-cyclopentadiene), diphenylsilylbis (1-indene), ethylenebis (1-indene), ethylenebis (trimethylcyclopentadiene), ethylenebis (5-dimethylamino- 1-indene), ethylenebis (6-dipropylamino-1-indene), ethylenebis (4,7-bis (dimethylamino)-1-indene), ethylenebis (5-diphenylphosphino-1-indene), ethylenebis-(4,5,6,7-tetrahydro-1-indene), ethylenebis (4-methyl-1-indene), ethylenebis (5-methyl-1-indene), ethylenebis (6-methyl-1-indene), ethylenebis (7-methyl-1-indene), ethylenebis (5-methoxy-1-indene), ethylenebis (4,7-di-methoxy-1-indene), ethylenebis (2,3-dimethyl-1-indene), ethylenebis 4,7-dimethyl-1-indene), ethylene bis (9-fluorene), and ethylene bis (1-cyclopentadiene).

According to the invention, the reaction mixture from the second step is reacted, preferably directly without isolation of the reaction product, in a third step again with one or more magnesium compounds of the formula $(R^3R^4)_cMg$ wherein $R^3,R^4$ and c are as defined for step 1), in preferably stoichiometric amounts under the same reaction conditions as in step 1) to give the bridged magnesium compounds $Q(CpR_a)_2Mg$.

Into this reaction mixture is metered a tin compound of the general formula $R_{4-k}^6SnX_k^3$ at temperatures between about 20° and 120° C., preferably at the reaction temperature of step 3.

In the tin compounds, $R^6$ is preferably an alkyl radical having 2–20 carbon atoms, in particular 4–8 carbon atoms, $X^3$ is a halogen radical, in particular Cl or Br, and k is from 1 to 4. According to the invention, preference is given to di-n-butyltin dichloride, tri-n-butyltin chloride, tri-n-octyl tin chloride or di-n-octyl tin dichloride. The tin compound is preferably used in twice the molar amount of the magnesium compound.

After the reaction is complete, after from 1 to 4 hours depending on reaction temperature, and after cooling to room temperature, all precipitated magnesium salts are separated off by the customary methods such as decantation, filtration and/or centrifugation.

In the fifth step, the solids-free organic phase, which contains the compound $Q(CpR_a)_2(SnX_{k-1}^3R_{4-k}^6)_2$ as reaction product, is (preferably without further workup) admixed at room temperature with the transition metal halide $M(X)_m$, wherein M is a metal of any of groups 3 to 6 of the Periodic Table of the Elements (IUPAC notation), in particular Zr or Hf, X is a halogen atom, in particular Cl or Br, and m is equal to the oxidation state of M, and the reaction is carried out at from room temperature up to the boiling point of the solvent used, preferably 20°–120° C., in particular 20°– 80° C. The reaction is generally complete after from 1 to 4 hours.

The reaction of the fifth step can lead to stereo-isomeric compounds which are obtained in racemic and mesomeric form. For the preparation of catalysts for olefin polymerization, preference is given to the racemic compounds because of their high activity and stereo-selectivity.

In place of the complicated processes, usual in the prior art, for isolating the racemates, in the process of the invention the ratio can be controlled in a simple manner by means of the selected concentration ratios alone:

The higher the concentration of tin compound, the higher the proportion of racemate.

To achieve the desired ratio of racemate (rac):meso compound, the solvent is, prior to the reaction with the transition metal halide, distilled off completely or partially, i.e. in the required amount.

According to the invention, the process is preferably carried out without isolation of the reaction products of the steps 1 to 4. However, it is likewise possible to isolate the respective intermediates prior to the reaction in the subsequent step or, if desired, to prepare them in another way and to use them for the subsequent step.

In the case of the unsymmetrical compounds $Q(CpR_a)(Cp'R'_{a'})$, in which $CpR_a$ is not the same as $Cp'R'_{a'}$, these are prepared by processes known in the literature and, commencing in step 3, are reacted further according to the process steps 3), 4) and 5) of the invention to give the metallocenes.

Unsymmetrical compounds which can be additionally used according to the invention are 2,2-propylbis( 1-indene) (1-cyclopentadiene), 2,2-propylbis (1-indene) (9-fluorene), diphenylmethylbis (1-indene) (1-cyclopentadiene), diphenylmethylbis (1-indene) (9-fluorene), diphenylsilylbis (1-indene) (1-cyclopentadiene), diphenylsilylbis (1-indene) (9-fluorene), ethylenebis (1-indene) (1-cyclopentadiene) and ethylenebis (1-indene) (9-fluorene).

EXAMPLES

All experiments were carried out with exclusion of oxygen and moisture under inert gas.

EXAMPLE 1

Preparation of Ethylenebis (inden-1-yl) Zirconium Dichloride a) Racemate (Rac):Meso=1:1

At room temperature (RT), a mixture was prepared of 556 ml BOMAG®-A (0,486 mol; a mixture of butyl and octylmagnesium from Witco GmbH; 20% strength in heptane) and 126 ml of indene (90% strength; 0.97 mol).

The mixture was subsequently stirred for 4 hours under reflux, until the cessation of gas evolution indicated completion of the reaction.

After cooling to 70° C., 41.9 ml (0.486 mol) of 1,2-dibromoethane and 69 ml of di-n-butyl ether were metered in. The mixture was again refluxed for 4 hours.

Prior to the addition of a further 556 ml of BOMAG®-A the reaction mixture was cooled to RT.

This was followed by refluxing for a further 3 hours.

264 ml (0.97 mol) of tri-n-butyltin chloride were then added to the cooled mixture.

Under reflux for a period of 2 hours, the tributyltin was substituted and magnesium chloride was eliminated.

After separating off the inorganic salts, the clear solution obtained was admixed with 102 g of $ZrCl_4$ (0.44 mol) and stirred for 1 hour at RT and for 3 hours at 60° C.

The crude product was then isolated by means of filtration.

Yield: 156 g of crude product (85% of theory, based on $ZrCl_4$; rac:meso ratio=1:1).

Boiling with fresh heptane and stirring with THF at RT gave 55 g (30%) of pure rac compound (I): Ethylene (indenyl)$_2$ZrCl$_2$: $^1$H-NMR: (CDCl$_3$; 7.23 ppm) 7.68–7.13 (m, 8H, C$_6$H$_4$); 6.58 (d, 2H, a—C$_5$H$_2$); 6.2 (d, 2H, b—C$_5$H$_2$); 3.75 (s, 4H, —CH$_2$CH$_2$—) Zr: calc. : 21.8%, found: 22.0%; Cl: calc. : 16.9%, found: 16.7% b) Rac:Meso= 10:1

The reaction was carried out in a similar way to 1 a), but with freeing the reaction solution of solvent (by heating up to 80° C./1 torr) prior to the addition of the ZrCl$_4$.

147 g (80%) of crude product having a rac:meso ratio of 10:1 were obtained. After purification, 110 g (60%) of pure rac compound were isolated.

($^1$H-NMR was identical with that in 1 a); Zr: 21.9%; Cl: 16.6%).

EXAMPLE 2

Preparation of Ethylenebis (inden-1-yl) Hafnium Dichloride a) Rac:Meso=2:1

85.2 ml of indene (94% strength; 0.73 mol) were initially charged and 416 ml of BOMAG®-A (20% strength in heptane; 0.364 mol) were metered in under reflux. The mixture was refluxed for 6 hours.

31.4 ml of 1,2-dibromoethane (0.364 mol) and 50 ml of di-n-butyl ether were added at 60°–70° C. and the mixture was allowed to react further for 4 hours under reflux.

Subsequently, another 416 ml of BOMAG®-A (20% strength in heptane; 0.364 mol) were introduced and the mixture was stirred for 4 hours under reflux.

196 ml of tri-n-butyltin chloride (0.723 mol) were then metered in at 80° C. with subsequent refluxing for 4 hours.

All inorganic salts were subsequently separated off and the clear filtrate was used further.

HfCl$_4$ (92.2 g; 0.288 mol) was introduced into the solution at 0° C. The mixture was slowly heated to 60° C. After 30 minutes the temperature was raised to reflux temperature and the reaction mixture was left thereat for 2 hours.

After cooling to RT, the solid which precipitated was isolated and dried.

110 g (92%) of crude product (II) having a rac:meso ratio of about 2:1 were isolated.

Stirring with tetrahydrofuran (THF) finally gave 50.2 g (42%) of pure racemate of (II).

rac-ethylene (indenyl)$_2$HfCl$_2$ (II):

$^1$H-NMR: (CDCl$_3$, 7,23 ppm)

7.65–7.1 (m, 8H, C$_6$H$_4$); 6.48 (d, 2H, a—C$_5$H$_2$); 6.09 (d, 2h, b—C$_5$H$_2$); 3.8 (s, 4H, —CH$_2$CH$_2$—)

Hf: calc.: 35.3%, found 35.8%; Cl: calc.: 14.02%, found: 13.9% b) Rac:Pure

The reaction was carried out in a similar way to 2 a), but after the reaction with tri-n-butyltin chloride and the removal of the precipitated inorganic salts the solution was freed of solvent by distillation with the application of vacuum.

The crude product obtained after reaction with HfCl$_4$ contained no meso compound.

After purification, 73.5 g (61% of theory; based on HfCl$_4$) of pure (II) were obtained by means of filtration and drying.

$^1$H-NMR identical with that in 3 a);

Hf: found 35.5 % Cl: found 14.0%

EXAMPLE 3

Preparation of Me$_2$Si-bis(inden-1-yl) Zirconium Dichloride a) Rac:Meso=1.1:1

55.7 ml of indene (95% strength; 0. 454 mol) and 50 ml of heptane were initially charged and admixed over a period of 15 minutes under reflux with 260 ml of BOMAG®-A (20% strength in heptane; 0,227 mol). After refluxing for 3 hours, the mixture was cooled to RT.

29.3 g of dimethydichlorosilane (0.227 mol), 39 ml of di-n-butyl ether and 25 ml of hexane were then metered into the reaction solution and the mixture was refluxed for 3 hours.

After adding further BOMAG®-A (260 ml; 0.227 mol), boiling for 4 hours under reflux and cooling to RT, 123 ml of tri-n-butyltin chloride were metered in while stirring (the temperature rose to 4520 C.) and the reaction was continued for 4 hours at 50° C.

The precipitated salts were separated off and the clear filtrate was admixed with 47.6 g of ZrCl$_4$ (0.204 mol).

The mixture was stirred for 2 hours at RT and for 1 hour under reflux.

Filtration and drying gave 79.7 g of crude product (87% of theory; based on ZrCl$_4$) having a rac:meso ratio of 1.1:1.

Purification gave a yield of pure rac product (III) of 28.4 g (31%).

rac-Me$_2$Si(indenyl)$_2$ZrCl$_2$ (III):

$^1$H-NMR:(CDCl$_3$, 7.23 ppm) 7.62–7.03 (m, 8H, C$_6$H$_4$; 6.94 (d, 2H, a—C$_5$H$_2$); 6.1 (d, 2H, b—C$_5$H$_2$); 1.13 (s, 6 H, Si(CH$_3$)$_2$) Zr: calc.: 20.3%, found: 20.3%; Cl: calc.: 15.8%, found: 15.7% b) Pure Racemate 522 ml of BOMAG®-A (20% strength; 456.6 mmol) were initially charged and heated to reflux. 121 ml of indene (90% strength:931.2 mmol) were then metered in over a period of 30 minutes with subsequent refluxing for 4 hours.

At RT, 55.3 ml of $Me_2SiCl_2$ (456 mmol), 80 ml of di-n-butyl ether and 40 ml of hexane were then added thereto. This was followed by refluxing for 2 hours.

After addition of 522 ml of BOMAG®-A and further reaction for 4 hours under reflux, tri-n-butyltin chloride (253 ml, 931 mmol) was metered in at RT and the mixture left at 50° C. for 4 hours.

The reaction solution was freed of the precipitated salts and volatile constituents were separated off by distillation (up to 100° C.; 1 torr).

98 g of $ZrCl_4$ (420 mmol) were introduced at 20° C. into the viscous, clear solution. The mixture was stirred for 2 hours at 90° C.

149 g of crude product (79% of theory; based on $ZrCl_4$), still containing small amounts of impurities but no meso compound, were obtained.

After purification, 122 g of pure rac (III) (65% of theory) were obtained. $^1$H-NMR identical with that in 3 a) Zr: found: 20.4% Cl: found 15.6%

EXAMPLE 4

Industrial Preparation of $Me_2Si(indenyl)_2ZrCl_2$ 7.95 kg of indene (90% strength) were initially charged into a 150 liter reactor and admixed with 27.05 kg of BOMAG®-A (1.2 mol/kg).

After heating to reflux (98° C.), the mixture was left for 3 hours at this temperature, until butane gas evolution had finished.

A solution of 4.24 kg of dichlorodimethylsilane and 4.23 kg of di-n-butyl ether in 4 liters of hexane was then metered at about 70° C. into the suspension obtained. This was followed by further reaction for 2 hours under reflux.

Immediately afterwards, a further 27.05 kg of BOMAG®-A was added with subsequent refluxing for 3 hours.

21.14 kg of tri-n-butyltin chloride were then metered in and the mixture was stirred for 3 hours at 50° C.

The precipitated magnesium salt was separated off by means of filtration and the filtrate was freed of solvent.

The remaining viscous solution was admixed, starting at RT, with 6.96 kg of zirconium tetrachloride and refluxed for a further 3 hours.

The crude product was subsequently isolated by means of filtration (pure rac compound; no meso compound detectable; crude yield 90%).

For further purification, the product was stirred further with THF, so that 75% (9.8 kg of clean rac-$Me_2Si(indenyl)_2ZrCl_2$) were finally obtained.

EXAMPLE 5

Preparation of $Me_2Si$-bis(inden-1-yl)hafnium Dichloride a) Rac:Meso=2:1

148.6 ml of BOMAG®-A (20% strength in heptane; 130 mmol and 33.8 ml of indene (90% strength; 260 mmol) were mixed together and refluxed for 4 hours.

15.8 ml of $Me_2SiCl_2$ (130 mmol), 20 ml of hexane and 20 ml of di-n-butyl ether were subsequently added at 20° C. The mixture was then refluxed for 3 hours.

The reaction mixture thus obtained was admixed with a further 148.6 ml of BOMAG®-A and refluxed for 3 hours, after which 70.5 ml of tri-n-butyltin chloride (260 mmol) were metered in at RT and the reaction was continued for a further 3 hours at 50° C. while stirring.

After removing the precipitated solids, the clear solution obtained was admixed with 37.5 g of $HfCl_4$ (117 mmol) and refluxed for 2 hours.

Filtration gave 44.5 g of crude product (IV) (71% of theory, based on $HfCl_4$) having a rac:meso ratio of 2:1. $Me_2Si(indenyl)_2HfCl_2$ (IV) $^1$H-NMR: ($CDCl_3$, 7.23 ppm) 7.58–7.03 (m, 8H, $C_6H_4$); 6.8 (d, 2H, $C_5H_2$); 6.05 (d, 2H, $C_5H_2$; 1.1 s, 6H, $Si(CH_3)_2$) Hf: calc.: 33.3%, found: 33.6%; Cl: calc.: 13.2%, found: 13.0% b) Pure Racemate

The reaction was carried out in a similar manner to Experiment 5 a), except that the reaction solution was freed of the solvent (heated up to 120° C./1 torr) prior to the addition of the $HfCl_4$.

This gave a meso-free crude product which, after purification, gave 43.9 g (70% of theory) of pure rac-metallocene (IV). $^1$H-NMR identical with that in 6 a) Hf: found: 33.4%; Cl: found: 13.3%

EXAMPLE 6

Use of Further Dialkylmagnesium Compounds a) The process steps in Example 3 a) were repeated, but using dibutylmagnesium (1 molar in heptane) in place of BOMAG®-A. The reflux times during the reaction of the dialkylmagnesium were here extended by 30 minutes in each case. 68 g of crude product $Me_2Si(indenyl) 2rCl_2$ (having a rac:meso ratio of 1:1) was obtained.

b) Example 3 a) was carried out using dihexylmagnesium (1 molar in heptane). 70 g of crude product $Me_2Si(indenyl)_2ZrCl_2$ (having a rac:meso ratio of 1:1) was obtained.

EXAMPLE 7

Isolation and Characterization of the Intermediate Ethylene(indenyl)$_2$ (tri-n-butyltin)$_2$ 10 g of indene (95% strength, 82 mmol) were admixed with 34.2 g of BOMAG®-A (20% strength in heptane; 41 mmol) and heated under reflux for 4 hours 7.7 g (41 mmol) of 1,2-dibromoethane and 5.3 g (41 mmol) of n-butyl$_2$O were then added at room temperature and the mixture was again stirred for 3 hours under reflux.

The precipitated $MgBr_2$ was subsequently separated off by means of filtration.

The filtrate was admixed with 34.2 g of BOMAG®-A (20% strength in heptane; 41 mmol) and refluxed for 4 hours.

26.8 g (82 mmol) of tri-n-butyltin chloride were subsequently added at 50° C. and the mixture was refluxed for a further 2 hours.

The precipitated $MgCl_2$ was separated off by filtration and the filtrate was evaporated to dryness (up to 100° C./1 mbar).

This gave Et(indenyl)$_2$TBT$_2$ (TBT=tri-n-butyl tin) in the form of a viscous oil in quantitative yield.

$^1$H-NMR: (CDCl$_3$) 7.55 (m, 2H); 7.45 (m, 2H); 7.3–7.1 (m, 4H); 6.5 (d, 2H), 4.02 (m, 2H); 3.02 (s, 4H); 1.7–1.1 (m, 36 H); 0.9–0.7 (m, 8 H).

EXAMPLE 8

Isolation and Characterization of the Intermediate Compound Me$_2$Si(indenyl)$_2$TBT$_2$ 12.2 g of indene (95% strength; 0.1 mol) were admixed with 41 g of BOMAG®-A (20% strength in heptane; 50 mmol) and refluxed for 4 hours.

6.45 g of Me$_2$SiCl$_2$ (50 mmol) and 6.5 g of n-butyl$_2$O (50 mmol) were subsequently added at room temperature and the mixture was again refluxed for 2 hours.

100 mmol (32.8 g) of tri-n-butyltin chloride were then added, the mixture was stirred under reflux for 2 hours, cooled, filtered and the filtrate was evaporated to dryness (100° C./1 mbar).

This gave Me$_2$Si(indenyl)$_2$TBT$_2$ as a viscous oil in quantitative yield. $^1$H-NMR: (CDCl$_3$) 7.6–7.3 (m); 7.2–6.9 (m); 4.25 (s, 2H); 1.8–1.1 (m, 36 H); 0.9–0.7 (m, 18 H); 0.5 (s, 6 H).

EXAMPLE 9

Isolation and Characterization of the Compound Me$_2$Si[(Me$_4$Cp)(tert-BuN)](tri-n-butyltin)$_2$: 13.25 g (53 mmol) of Me$_2$Si[(Me$_4$CpH)(tert-BuNH)]

(Literature: Organometallics, 1990, 9, 867) were added to 63.6 ml of BOMAG®-A (53 mmol) and the mixture was refluxed for 3 hours.

The solution was subsequently cooled to –40° and a solid precipitated which was isolated (13.9 g). Me$_2$Si [(Me$_4$Cp)(tert-BuN)]Mg: $^1$H-NMR: (DMSO) 1.99 (s, 6 H, b-Me$_2$Cp); 1.79 (s, 6 H, a-Me$_2$Cp); 1.09 (s, 9 H, Me$_3$C); 0.12 (s, 6 H, SiMe$_2$)

10 g of Me$_2$Si[(Me$_4$Cp)(tert-BuN)]Mg (36.5 mmol) were dissolved in 50 ml of xylene and admixed with tri-n-butyltin chloride (73 mmol; 23.8 g) and the mixture was refluxed for 5 hours.

The xylene was drawn off from the solution obtained after filtration and the remaining viscous oil was analyzed by means of NMR spectroscopy, $^1$H-NMR: (CDCl$_3$) 1.98 (s, 6H, a—Me$_2$Cp); 1.82 (s, 6 H, Me$_2$Cp); 1.7–1.6 (m, 12 H, Sn—CH$_2$—); 1.43– 1.1 (m, 24 H, —CH$_2$CH$_2$—); 1.06 (s, 9 H, Me$_3$C); 0.95 (t, 18 H, H$_3$C—); 0.09 (s, 6 H, Me$_2$Si).

What is claimed is:

1. A compound of the general formula $$Q(CpR_a)(Cp'R'_{a'})(SnX_{k-1}^3R_{4-k}^6)_2$$

wherein Q is a single-membered or multi-membered bridge

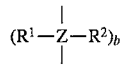

between Cp and Cp', wherein each R$^1$ and R$^2$ are identical or different and each is a hydrogen atom, a C$_1$–C$_{10}$ alkyl group or a C$_6$–C$_{10}$ aryl group, Z is carbon, silicon or germanium, and b is 1, 2 or 3; 0≦a≦4 and 0≦a'≦4;

Cp and Cp' are each a cyclopentadienyl, an indenyl or a fluorenyl radical;

R and R' are the same or different and in each occurrence is an alkyl, alkoxy, phosphine, amino, alkylamino, dialkylamino, alkoxy-alkyl, aryl-alkyl, or aryloxy-alkyl group;

R$^6$ is a C$_2$–C$_{20}$-alkyl radical or a C$_6$–C$_{10}$-aryl radical;

k is 1–4; and

X$^3$ is a halogen atom.

2. A compound according to claim 1 wherein R and R' are each selected from the group consisting of alkyl containing 1 to 10 carbon atoms, alkoxy containing 1 to 10 carbon atoms, alkylamino containing 1 to 10 carbon atoms, dialkylamino wherein each alkyl group contains 1 to 10 carbon atoms, alkoxyalkyl containing a total of 2 to 20 atoms, C$_6$–C$_{10}$-aryl-C$_1$–C$_{10}$ alkyl, C$_6$–C$_{10}$-aryloxy-C$_1$–C$_{10}$-alkyl, and phosphine.

3. A compound according to claim 2 wherein R and R' are each selected from the group consisting of methyl, ethyl, methoxy, ethoxy, dimethylamino, dipropylamino, dialkylphosphine and diphenylphosphine.

4. A compound according to claim 1 wherein R$^1$ and R$^2$ are each selected from the group consisting of C$_1$–C$_5$ alkyl and C$_6$–C$_8$ aryl.

5. A compound according to claim 4 wherein R$^1$ and R$^2$ are each selected from the group consisting of methyl, ethyl and phenyl.

6. A compound according to claim 1 wherein R$^6$ is alkyl containing 4 to 8 carbon atoms.

7. A compound according to claim 1 wherein X$^3$ is Cl or Br.

8. A compound according to claim 1 wherein a'=1 and Cp'R'=NR" wherein R" is a C$_1$–C$_{12}$ alkyl or C$_6$–C$_{12}$ aryl radical.

* * * * *

UNITED STATES PATENT AND TRADEMARK OFFICE
CERTIFICATE OF CORRECTION

PATENT NO. : 5,543,535

DATED : August 6, 1996

INVENTOR(S) : Richard Kisowsky

It is certified that error appears in the above-identified patent and that said Letters Patent is hereby corrected as shown below:

Column 3, line 54: delete "6"
Column 6, line 62: "0,486" should read --0.486--
Column 8, line 4: "7,23" should read --7.23--
Column 8, line 23: "CI" should read --C1--
Column 8, line 36: "0,227" should read --0.227--
Column 8, line 45: "4520 C.)" should read --45 C.)--

Column 10, line 65: "/1 mbar)" should read --/0.1 mbar)--
Column 11, line 19: "/1 mbar)" should read --/0.1 mbar)--

Signed and Sealed this

Sixth Day of May, 1997

Attest:

BRUCE LEHMAN

Attesting Officer    Commissioner of Patents and Trademarks